(12) United States Patent
Raymond et al.

(10) Patent No.: US 10,801,829 B2
(45) Date of Patent: Oct. 13, 2020

(54) SIGNAL EXTRACTION SYSTEMS AND METHODS

(71) Applicant: AMO Development, LLC, Santa Ana, CA (US)

(72) Inventors: Thomas D. Raymond, Edgewood, NM (US); Isaac Neal, Tijeras, NM (US); Daniel R. Hamrick, Cedar Crest, NM (US); Thomas M. Shay, St. George, UT (US)

(73) Assignee: AMO Development, LLC, Santa Ana, CA (US)

( * ) Notice: Subject to any disclaimer, the term of this patent is extended or adjusted under 35 U.S.C. 154(b) by 16 days.

(21) Appl. No.: 16/179,743

(22) Filed: Nov. 2, 2018

(65) Prior Publication Data

US 2019/0072376 A1 Mar. 7, 2019

Related U.S. Application Data

(63) Continuation of application No. 15/342,418, filed on Nov. 3, 2016, now Pat. No. 10,119,803.
(Continued)

(51) Int. Cl.
*G01B 9/02* (2006.01)
*A61B 3/10* (2006.01)
*A61B 3/00* (2006.01)

(52) U.S. Cl.
CPC ........ *G01B 9/02083* (2013.01); *A61B 3/0025* (2013.01); *A61B 3/102* (2013.01);
(Continued)

(58) Field of Classification Search
CPC ............ G01B 9/02083; G01B 9/02004; G01B 9/0204; G01B 9/02091; A61B 3/0025; A61B 3/102
See application file for complete search history.

(56) References Cited

U.S. PATENT DOCUMENTS 7,006,772 B2 * 2/2006 Kuri ....................... H04B 10/50
398/202
7,860,406 B2 * 12/2010 Xie ........................ H04B 10/671
398/203

(Continued)

OTHER PUBLICATIONS

Biedermann B.R., et al., "Real Time en face Fourier-Domain Optical Coherence Tomography with Direct Hardware Frequency Demodulation," Optics Letters, 2008, vol. 33 (21), pp. 2556-2558.
(Continued)

*Primary Examiner* — Freshteh N Aghdam
(74) *Attorney, Agent, or Firm* — Johnson & Johnson Surgical Vision, Inc.

(57) ABSTRACT

Swept source optical coherence tomography (SS-OCT) systems and methods may employ down-conversion. Down-converter systems and methods may utilize a distribution element and a frequency down shifter. The distribution element may receive an output signal of a photo detection device, the output signal comprising a first frequency component at or below a maximum conversion frequency and a second frequency component above the maximum conversion frequency. The distribution element may send the first frequency component to an analog to digital (A/D) converter and send the second frequency component to a frequency down shifter. The frequency down shifter may down shift the second frequency component to a frequency at or below the maximum conversion frequency to form a down shifted second frequency component. The frequency down shifter may send the down shifted second frequency component to the A/D converter.

20 Claims, 9 Drawing Sheets

Related U.S. Application Data

(60) Provisional application No. 62/250,433, filed on Nov. 3, 2015.

(52) U.S. Cl.
CPC ..... *G01B 9/02004* (2013.01); *G01B 9/02041* (2013.01); *G01B 9/02091* (2013.01)

(56) References Cited

U.S. PATENT DOCUMENTS

| | | | |
|---|---|---|---|
| 8,374,514 B2* | 2/2013 | Huang | H04B 10/60 398/163 |
| 9,209,908 B2* | 12/2015 | Yu | H04B 10/614 |
| 2010/0002226 A1 | 1/2010 | Hartog | |
| 2012/0120757 A1 | 5/2012 | Deal et al. | |
| 2013/0271772 A1 | 10/2013 | Johnson et al. | |
| 2014/0024947 A1 | 1/2014 | Barbato | |
| 2014/0071456 A1 | 3/2014 | Podoleanu et al. | |
| 2014/0270803 A1* | 9/2014 | Olsson | H04B 10/532 398/152 |
| 2015/0037877 A1 | 2/2015 | Peng et al. | |
| 2016/0006453 A1* | 1/2016 | Jalali | H03M 5/22 341/87 |
| 2016/0252340 A1 | 9/2016 | Hollenbeck et al. | |

OTHER PUBLICATIONS

International Search Report and Written Opinion for Application No. PCT/US2016/060281, dated Feb. 10, 2017, 15 pages.

Koch P., et al., "Linear Optical Coherence Tomography System with a Downconverted Fringe Pattern," Optics Letters, 2004, vol. 29 (14), pp. 1644-1646.

Lee H.Y., et al., "Interleaved Optical Coherence Tomography," Optics Express, 2013, vol. 21 (22), pp. 26542-26556.

Maheshwari A., et al., "Heterodyne Swept-Source Optical Coherence Tomography for Complete Complex Conjugate Ambiguity Removal," Department of Biomedical Engineering, 2005, 5 pages.

\* cited by examiner

SIGNAL EXTRACTION SYSTEMS AND METHODS

CROSS-REFERENCE

This application is a continuation of co-pending U.S. patent application Ser. No. 15/342,418, filed on 3 Nov. 2016, and also claims the benefit under 35 U.S.C. § 119(e) of U.S. Provisional Patent Application No. 62/250,433, filed Nov. 3, 2015, the full disclosures of each of which applications are incorporated herein by reference.

TECHNICAL FIELD

Embodiments disclosed herein may pertain to signal processing in optical measurement systems and, more particularly, to optical coherence tomography signal processing.

BACKGROUND

Optical coherence tomography may be used in a variety of medical applications. One method, swept source optical coherence tomography (SS-OCT) or optical frequency domain imaging (OFDI), as it is sometimes called, is used often for its simplicity, flexibility, and signal to noise ratio.

An example SS-OCT (or OFDI) system 100 is illustrated in FIG. 1. The swept source 110 is a narrow bandwidth laser whose frequency is swept in time. The output of the swept source 110 is directed to a beam splitter 120 that directs some of the light to a reference path 124 and some of the light to the sample path 122. The reference path 124 may include some optional elements 130 such as dispersion compensation elements and/or path length changing elements in some designs. The light in the sample path 122 is directed to the sample 10 under investigation by light delivery and collection optics 140, and the light backscattered from the sample 10 under investigation is collected by the light delivery and collection optics 140. The light backscattered by the sample 10 is then combined with the light from the reference path 124 in the beam combiner 150 and directed to a photo detector 160 where the interference signal between the two optical fields is detected. The interference signal from the photo detector 160 is directed to the analog to digital (A/D) converter 170. Finally, the output of the A/D converter 170 is sent to the data analysis system (DAS) 180.

The electrical fields from the reference beam 124, $E_r(t)$ and the electrical field backscattered from the sample 10, $E_s(t)$ are $$E_r(t) = E_{r0} e^{-i2\pi \nu(t) t} \text{ and} \qquad (1)$$

$$E_s(t) = \Sigma_n E_{sn} e^{-i2\pi \nu(t+\tau_n)(t+\tau_n)} \qquad (2)$$

where $E_{r0}$ represents the reference beam 124 electric field amplitude at the photo detector 160, and $E_{sn}$ represents the electric field amplitude of the backscattering from $n^{th}$ sample 10 element. $\nu(t)$ represents the laser frequency at the photo detector 160 at time t, and the $\nu(t+\tau_n)$ represents the $n^{th}$ sample 10 element backscattered laser frequency at the photo detector 160 at time $t+\tau_n$. $\tau_n$ represents the time delay between the reference beam 124 and the time when the backscattering from element n of the sample 10 arrives at the photo detector 160. The summation in Eq. 2 is over all of the n sample 10 spatial elements.

The interference signal between the reference light 124 and the light backscattered by a sample 10 on the photo detector 160 produces a signal proportional to the product of the reference field amplitude times, the backscattered field amplitude from the spatial elements in the sample 10 at the sum, and difference frequencies between the reference field frequency and backscattered sample 10 element frequency, $$V_{PD}(t) \propto \Sigma_n [|\Sigma_{r0}||E_{sn}|e^{-i2\pi[\nu(t)-(t+\tau_n)]t} + |E_{r0}| \\ |E_{sn}|e^{-i2\pi[\nu(t)+(\nu(t+\tau_n))]t}] \qquad 3)$$

or $$V_{PD}(t) = \Sigma_n [V_{PD\_n\_amp}(e^{-i2\pi[\nu(t)-(\nu(t+\tau_n))]t} + \\ e^{-i2\pi[\nu(t)+(\nu(t+\tau_n))]t})], \qquad 4)$$

where $V_{PD\_n\_amp}$ represents the signal amplitude generated by the photo detector 160 due to the interference between the $n^{th}$ sample 10 element backscattering and the reference beam 124. The first term in the summation on the right hand side of Eq. 4 represents the unique beat note signal generated by the frequency difference for the $n^{th}$ spatial element. The second term in Eq. 4 represents the sum of two optical frequencies. Optical frequencies are many orders of magnitude too fast for electrical photo detectors 160 to detect. Therefore, the sum frequency term is integrated to zero by the photo detector 160, and hence the detected interference signal due to the all of the sample element 10 backscattering is given by, $$V_{PD}(t) = \Sigma_n [V_{PD\_n\_amp} e^{-i2\pi[\nu(t)-(\nu(t+\tau_n))]t}] \qquad 5)$$

The photo detector 160 signal due to the $n^{th}$ sample 10 element is, $$V_{PD\_n}(t) = V_{PD\_n\_amp} e^{-i2\pi[\nu(t)-(\nu(t+\tau_n))]t} \qquad 6)$$

From Eq. 6 it is clear that the $n^{th}$ sample 10 element produces a sinusoidal oscillation at a frequency, $$\nu_{fringe\_n} = \nu(t) - \nu(t+\tau_n) \qquad 7)$$

where, $\nu_{fringe\_n}$ is uniquely determined by the time delay between the reference path 124 and the $n^{th}$ sample 10 element path, $\tau_n$. If the sample 10 is stationary during the measurement, then the spatial elements can be uniquely located in space by the fringe frequencies. For the human eye to be considered stationary, these measurements need to be completed in under 0.2 seconds. For full 3-D medical scan of the human eye, approximately two thousand or more A-scans must be performed within 0.2 seconds. These requirements result in fringe frequencies that can easily exceed 1 GHz. For example, assuming 2000 A-scans are needed to measure the human eye, then every A-scan must be completed in less than 5 microseconds. The depth of a common human eye, $d_{eye}$ can be as high as 35 mm, which corresponds to a maximum time delay of, $$\tau_{max} = \frac{2 d_{eye} n_{eye}}{c} = 0.31 \text{ ns}, \qquad 8)$$

where, $n_{eye}$ represents the index of refraction of the eye at 1050-nm, and c represents the speed of light in vacuum. Typical swept frequency lasers are tuned around a center wavelength of $\lambda$ over spectral range, $\Delta\lambda$. Assuming a laser center wavelength of 1050-nm, a spectral sweep range of 100-nm and a linear frequency swept, then the maximum fringe frequency is, $$\nu_{fringe\_n\_max} = \frac{d\nu}{dt} \tau_{max} = \frac{c \Delta \lambda}{\lambda^2} \frac{1}{T_{Ascan}} \tau_{max}, \qquad 9)$$

where $v_{fringe\_n\_max}$ represents the highest fringe frequency generated in a full measurement of a human eye, and $T_{Ascan}$ represents the time for one A-scan. Note that higher fringe frequencies are present if the laser scan is nonlinear. For the characteristic human eye and swept source OCT specifications listed above, $$v_{fringe\_n\_max} = 1.7 \text{ GHz} \qquad 10)$$

The minimum sampling rate required to accurately reconstruct a noiseless uniformly sampled sinusoid is theoretically a minimum of twice $v_{fringe\_n\_max}$ according to the Nyquist criterion. If there are interfering signals, noise, and/or non-uniform sampling, then the sample rate must be significantly higher than twice $v_{fringe\_n\_max}$. In the case of SS-OCT, there is usually non-uniform sampling due to imperfection in the k-clock and considerable interference from the other fringe frequencies, $v_{fringe\_n}$, for example. Even if the laser's instantaneous coherence length limits the maximum measurable time delay to approximately ¼ the length of the human eye, the sampling rate of the analog to digital converter still needs to be significantly higher than the Nyquist rate of 0.8 Gsps. In addition, because of the multitude of signals simultaneously generated by the SS-OCT system, the analog to digital converters must have 12-bit resolution. High-resolution analog to digital converters with 1 giga samples per second (Gsps) rate are often more than a factor of ten more costly than ½ Gsps high resolution analog to digital converters.

In electronics, a mixer or frequency mixer is a nonlinear electrical circuit that creates new frequencies from two signals applied to it. In the most common application, two signals at frequencies $v_1$ and $v_2$ are applied to a mixer, and the mixer produces new signals at the sum $v_1+v_2$ and difference $v_1-v_2$ of the original frequencies. Mixers are widely used to shift signals from one frequency range to another, a process known as heterodyning. When the useful signal is contained in the difference frequency mixed signal, it is said to be down shifted or down converted. Such mixers often comprise nonlinear components such as diodes.

A well-known application of down conversion is the reception of FM radio broadcast signals; these are broadcast at around 100 MHz but contain audio information below 20 KHz. A local oscillator in the radio receiver produces a signal at the broadcast frequency (the tuner) which is mixed with the received signal; the difference frequency is then low pass filtered to produce the audio content.

SUMMARY OF THE DISCLOSURE

Hence, to obviate one or more problems due to limitations and disadvantages of the related art, this disclosure provides embodiments of signal extraction systems and methods applicable to swept source optical coherence tomography that may down shift the highest fringe frequencies to within the operating range of data acquisition systems. Several methods may allow the utilization of slower and much less expensive analog to digital converters for accurate reconstruction of higher OCT fringe frequencies as well as lower frequency OCT fringe frequencies. In some embodiments, there is no degradation in signal collection efficiency. The entire fringe frequency spectrum, limited only by the coherence length of the swept source, may be captured in a single A-scan.

An illustrative SS-OCT system according to some embodiments may include a down-converter system, the down converter system comprising a distribution element configured to receive an output signal of a photo detection device, the output signal comprising a first frequency component at or below a maximum conversion frequency and a second frequency component above the maximum conversion frequency; send the first frequency component to an A/D converter; and send the second frequency component to a frequency down shifter. The down converter system may also comprise the frequency down shifter, which may be configured to down shift the second frequency component to a frequency at or below the maximum conversion frequency to form a down shifted second frequency component; and send the down shifted second frequency component to the A/D converter.

In some embodiments, the system may further comprise a low noise amplifier coupled to the distribution element and configured to receive an unfiltered output signal of the photo detection device; filter the unfiltered output signal to generate the output signal; and send the output signal to the distribution element.

In some embodiments, the output signal may be received directly from the photo detection device.

In some embodiments, the distribution element may comprise a switch configured to switch to a first output to pass the first frequency component to the A/D converter during a first scan; and switch to a second output to pass the second frequency component to the frequency down shifter during a second scan. A bandpass filter or a highpass filter may be coupled between the second output of the switch and an input of the frequency down shifter. A second switch may be coupled to the first output of the switch and an output of the frequency down shifter, the second switch being configured to send an output of the second switch to the A/D converter. A buffer amplifier may be interposed between the A/D converter on an output side and the switch and the frequency down shifter on an input side.

In some embodiments, the distribution element may comprise a splitter configured to substantially simultaneously send the output signal to the A/D converter and to the frequency down shifter. The splitter may be an RF power splitter. A bandpass filter or a lowpass filter may be coupled between an output of the splitter and an input of the A/D converter. A bandpass filter or a highpass filter may be coupled between an output of the splitter and an input of the frequency down shifter. In some embodiments, the A/D converter comprises a plurality of separate A/D converters; and the A/D converter to which the down shifted second frequency component is sent is separate from the A/D converter to which the first frequency component is sent.

In some embodiments, the system may further comprise a plurality of filters, wherein the A/D converter comprises a plurality of separate A/D converters; the frequency down shifter comprises a plurality of separate frequency down shifters; the distribution element comprises a splitter configured to substantially simultaneously send the output signal to each of the plurality of filters; at least one of the filters comprises a lowpass filter or a bandpass filter coupled between a first output of the splitter and an input of a first one of the A/D converters; at least two of the filters comprise a highpass filter or a bandpass filter, each of the at least two filters being coupled between a separate output of the splitter and a separate frequency down shifter; and each separate frequency down shifter comprises an output coupled to a separate A/D converter. The splitter may be an RF power splitter. Each separate frequency down shifter may be configured to shift a separate portion of the second frequency component. Each of the filters may be configured to pass a different portion of the output signal.

In some embodiments, the system may further comprise a plurality of filters, wherein the frequency down shifter comprises a plurality of separate frequency down shifters; the distribution element comprises a first switch configured to sequentially send the output signal to each of the plurality of filters; and a second switch comprising an output coupled to the A/D converter; at least one of the filters comprises a lowpass filter or a bandpass filter coupled between a first output of the first switch and a first input of the second switch; at least two of the filters comprise a highpass filter or a bandpass filter, each of the at least two filters being coupled between a separate output of the first switch and a separate frequency down shifter; each separate frequency down shifter comprises an output coupled to a separate input of the second switch; and the second switch is configured to sequentially send a signal on each second switch input to the A/D converter. In some embodiments, each separate frequency down shifter may be configured to shift a separate portion of the second frequency component. In some embodiments, each of the filters may be configured to pass a different portion of the output signal.

In some embodiments, the distribution element may comprise a plurality of filters, wherein the distribution element comprises a first switch configured to sequentially send the output signal to each of the plurality of filters; a second switch comprising a plurality of inputs each coupled to one of the plurality of filters; and an output coupled to an input of the frequency down shifter; and a third switch comprising a second input coupled to an output of the frequency down shifter; and an output coupled to the A/D converter; at least one of the filters comprises a lowpass filter or a bandpass filter coupled between a first output of the first switch and a first input of the third switch; at least two of the filters comprise a highpass filter or a bandpass filter, each of the at least two filters being coupled between a separate output of the first switch and a separate input of the second switch; the second switch is configured to sequentially send a signal on each second switch input to the frequency down shifter; and the third switch is configured to sequentially send a signal on the first third switch input and a plurality of sequential signals on the second third switch input to the A/D converter. In some embodiments, each of the filters may be configured to pass a different portion of the output signal.

In some embodiments, the frequency down shifter may comprise a local oscillator; a mixer configured to receive the second frequency component and an output of the local oscillator and mix the received signals to form an intermediate output; and a lowpass filter or a bandpass filter coupled to an output of the mixer and configured to filter the intermediate output to produce the down shifted second frequency component. In some embodiments, the local oscillator may be configured to vary the frequency of the local oscillator output.

The system may further comprise at least one of the photo detection device, the A/D converter, and a data analysis system coupled to an output of the A/D converter.

An illustrative SS-OCT method according to some embodiments may include performing down-conversion via a down-conversion method comprising receiving, a distribution element, an output signal of a photo detection device, the output signal comprising a first frequency component at or below a maximum conversion frequency and a second frequency component above the maximum conversion frequency; sending, with the distribution element, the first frequency component to an analog to digital (A/D) converter; sending, with the distribution element, the second frequency component to a frequency down shifter; down shifting, with the frequency down shifter, the second frequency component to a frequency at or below the maximum conversion frequency to form a down shifted second frequency component; and sending, with the frequency down shifter, the down shifted second frequency component to the A/D converter.

In some embodiments, the method may further comprise receiving, at a low noise amplifier coupled to the distribution element, an unfiltered output signal of the photo detection device; filtering, with the low noise amplifier, the unfiltered output signal to generate the output signal; and sending, with the low noise amplifier, the output signal to the distribution element.

In some embodiments, the output signal may be received directly from the photo detection device.

In some embodiments, the method may further comprise switching, with a switch, to a first switch output to pass the first frequency component to the A/D converter during a first scan; and switching, with the switch to a second switch output to pass the second frequency component to the frequency down shifter during a second scan. In some embodiments, the method may further comprise filtering, with a bandpass filter or a highpass filter, a signal between the second output of the switch and an input of the frequency down shifter.

In some embodiments, the method may further comprise substantially simultaneously sending, with a splitter of the distribution element, the output signal to the A/D converter and to the frequency down shifter. In some embodiments, the method may further comprise filtering, with a bandpass filter or a lowpass filter, a signal between an output of the splitter and an input of the A/D converter. In some embodiments, the method may further comprise filtering, with a bandpass filter or a highpass filter, a signal between an output of the splitter and an input of the frequency down shifter. In some embodiments, the A/D converter comprises a plurality of separate A/D converters; and the A/D converter to which the down shifted second frequency component is sent is separate from the A/D converter to which the first frequency component is sent.

In some embodiments, wherein the A/D converter comprises a plurality of separate A/D converters and the frequency down shifter comprises a plurality of separate frequency down shifters, the method may further comprise substantially simultaneously sending, with a splitter of the distribution element, the output signal to each of a plurality of filters; filtering, with at least one of the filters comprising a lowpass filter or a bandpass filter, a signal between a first output of the splitter and an input of a first one of the A/D converters; filtering, with at least two of the filters comprising a highpass filter or a bandpass filter, each of at least two signals between separate outputs of the splitter and separate frequency down shifters, respectively; and outputting, with each separate frequency down shifter, separate signals to separate A/D converters, respectively. In some embodiments, the method may further comprise shifting, with each separate frequency down shifter, a separate portion of the second frequency component. In some embodiments, the method may further comprise passing, with each of the filters, a different portion of the output signal.

In some embodiments, wherein the frequency down shifter comprises a plurality of separate frequency down shifters, the method may further comprise sequentially sending, with a first switch of the distribution element, the output signal to each of a plurality of filters; filtering, with at least one of the filters comprising a lowpass filter or a bandpass filter, a signal between a first output of the first switch and a first input of a second switch of the distribution element; filtering, with at least two of the filters comprising a highpass filter or a bandpass filter, each of at least two signals between separate outputs of the first switch and separate frequency down shifters, respectively outputting, with each separate frequency down shifter, separate signals to separate inputs of the second switch, respectively; and sequentially sending, with the second switch, a signal on each second switch input to the A/D converter. In some embodiments, the method may further comprise shifting, with each separate frequency down shifter, a separate portion of the second frequency component. In some embodiments, the method may further comprise further comprising passing, with each of the filters, a different portion of the output signal.

In some embodiments, the method may further comprise sequentially sending, with a first switch of the distribution element, the output signal to each of a plurality of filters; filtering, with at least one of the filters comprising a lowpass filter or a bandpass filter, a signal between a first output of the first switch and a first input of a third switch of the distribution element; filtering, with at least two of the filters comprising a highpass filter or a bandpass filter, each of at least two signals between separate outputs of the first switch and separate inputs of a second switch of the distribution element, respectively; sequentially sending, with the second switch, a signal on each second switch input to the frequency down shifter; and sequentially sending, with the third switch, a signal on the first third switch input and a plurality of sequential signals on the second third switch input to the A/D converter. In some embodiments, the method may further comprise passing, with each of the filters, a different portion of the output signal.

In some embodiments, down shifting the second frequency component may comprise generating, with a local oscillator of the frequency down shifter, an output; receiving, at a mixer of the frequency down shifter, the second frequency component and the output of the local oscillator; mixing, with the mixer, the received signals to form an intermediate output; and filtering, with a lowpass filter or a bandpass filter coupled to an output of the mixer, the intermediate output to produce the down shifted second frequency component. In some embodiments, the method may further comprise varying the frequency of the local oscillator output.

This summary and the following detailed description are merely exemplary, illustrative, and explanatory, and are not intended to limit, but to provide further explanation of the invention as claimed. Additional features and advantages of the invention will be set forth in the descriptions that follow, and in part will be apparent from the description, or may be learned by practice of the invention. The objectives and other advantages of the invention will be realized and attained by the structure particularly pointed out in the written description, claims and the appended drawings.

BRIEF DESCRIPTION OF THE DRAWINGS

The novel features of the invention are set forth with particularity in the appended claims. A better understanding of the features and advantages will be facilitated by referring to the following detailed description that sets forth illustrative embodiments using principles of the invention, as well as to the accompanying drawings, in which like numerals refer to like parts throughout the different views. Like parts, however, do not always have like reference numerals. Further, the drawings are not drawn to scale, and emphasis has instead been placed on illustrating the principles of the invention. All illustrations are intended to convey concepts, where relative sizes, shapes, and other detailed attributes may be illustrated schematically rather than depicted literally or precisely.

DETAILED DESCRIPTION OF SEVERAL EMBODIMENTS

Systems and methods described herein may be used for down-converting SS-OCT fringe frequencies down to frequencies that can be reliably sampled by slow A/D converters.

Figure 1:
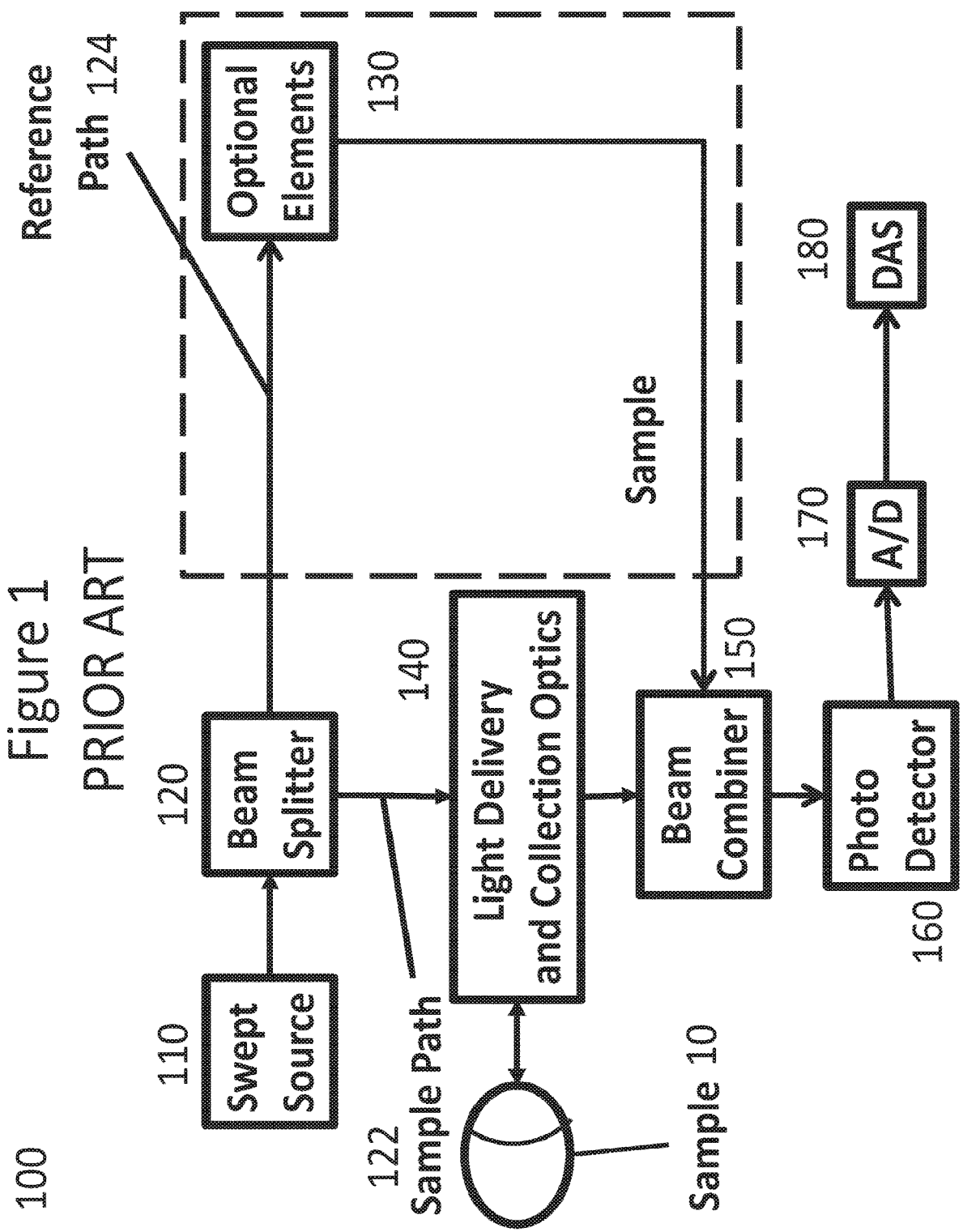
FIG. 1 is a block diagram of an example SS-OCT system.
Figure 2:
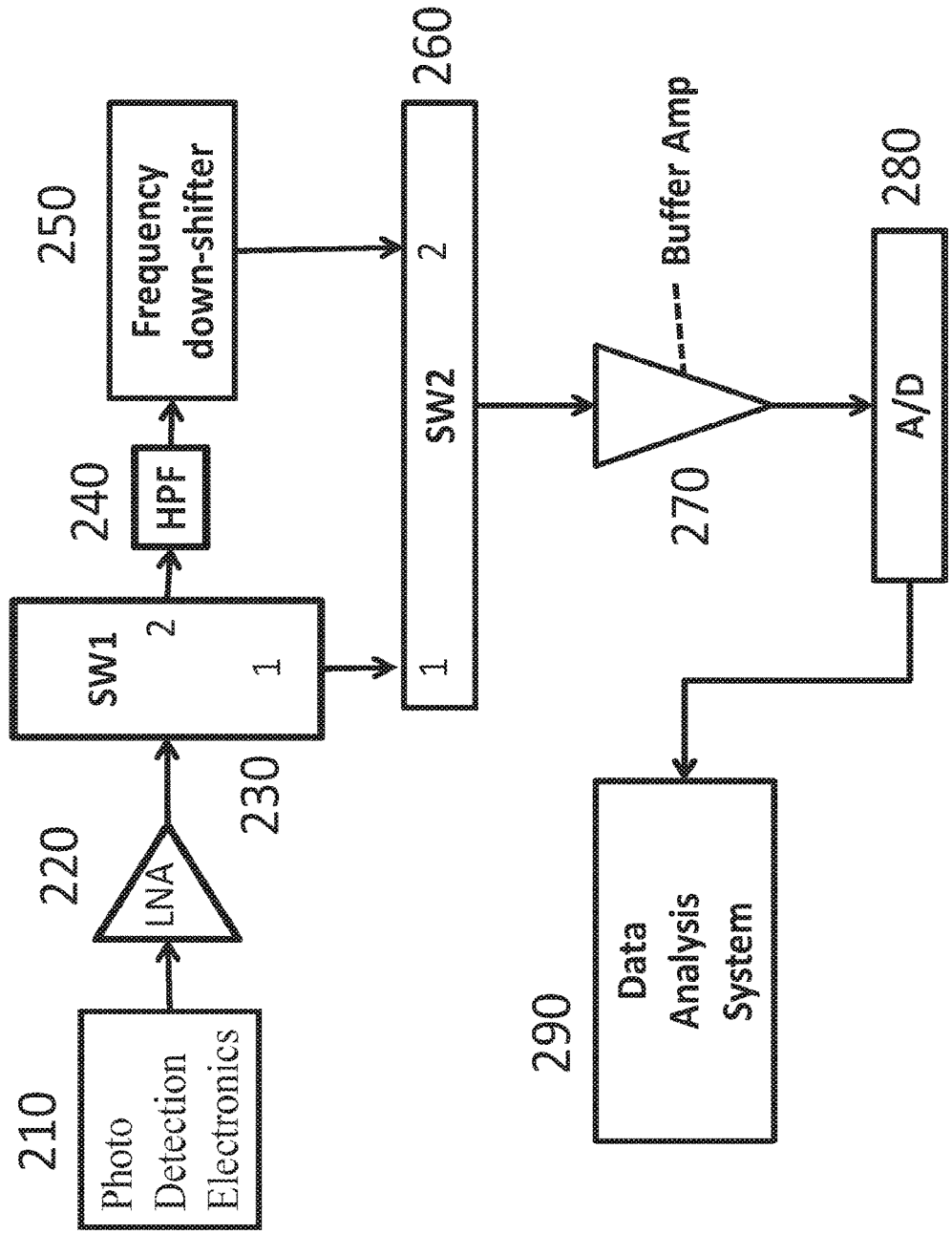
FIG. 2 is a block diagram of a down-converter system according to an embodiment of the invention.

FIG. 2 is a block diagram of a down-converter system 200 according to an embodiment of the invention. Signals from the photo detector electronics 210 may be amplified by an RF low noise amplifier (LNA) 220, and the amplified signals may be directed to the first switch SW1 230.

Some embodiments may omit the LNA 220 and send the output of the photo detector electronics 210 directly to the first switch SW1 230. When SW1 230 is in position 1, the signal may bypass the down-shifter system 250 and flow directly to the A/D converter 280 through SW2 260 in position 1, so that the output of the down-shifter system 250 is disconnected from the A/D converter 280. When SW1 230 is in position 2, the signal may be connected to a high pass filter (HPF) 240. The HPF 240 may attenuate frequencies below a predetermined value and send its output to the down-shifter system 250. A down-shifted output of the down-shifter system 250 may be connected to the A/D converter 280 via SW2 260 in position 2. A buffer amplifier 270 may be interposed between SW2 260 and A/D converter 280 to prevent the A/D converter 280 from loading the down-shifter system 250. SW2 260 may be provided in embodiments wherein SW1 230 does not provide satisfactory isolation between the input and output 1 of SW1 230 when the signal is connected to the down-shifter system 250 (i.e., when SW1 230 is in position 2). Thus, in some embodiments, SW2 260 may be omitted, and output 1 of SW1 230 and the output of the down-shifter system 250 may both be directly connected to A/D 280 (or buffer amplifier 270 if provided). Consider an OCT fringe frequency spectrum with a bandwidth, $$v_{fringe\_n\_max} \leq 2\ BW_{AtoD} \qquad\qquad 11)$$

where $BW_{AtoD}$ represents the maximum frequency sinusoid that the analog to digital converter can sample and result in accurate reconstruct of the original OCT signal after signal processing. The entire spectrum may be measured using the SS-OCT system 200 if the portion of the OCT fringe frequency spectrum above $BW_{AtoD}$ is down-shifted to less than or equal to $BW_{AtoD}$.

In the example embodiment of FIG. 2, two sequential A-scans may be used to capture the entire OCT fringe frequency spectrum, e.g., one A-scan with SW1 230 and SW2 260 both in position 1 for OCT fringe frequencies less than or equal to $BW_{AtoD}$ and a second A-scan with SW1 230 and SW2 260 both in position 2 to capture the high frequency OCT fringe frequency spectrum from fringe frequencies that are between $BW_{AtoD}$ and 2 $BW_{AtoD}$ before down-converting. The DAS 290 may receive the output of the A/D converter 280 for each scan, store the data from the low and high frequency scans separately, and reconstruct the original OCT spectrum from the received data.

Figure 3:
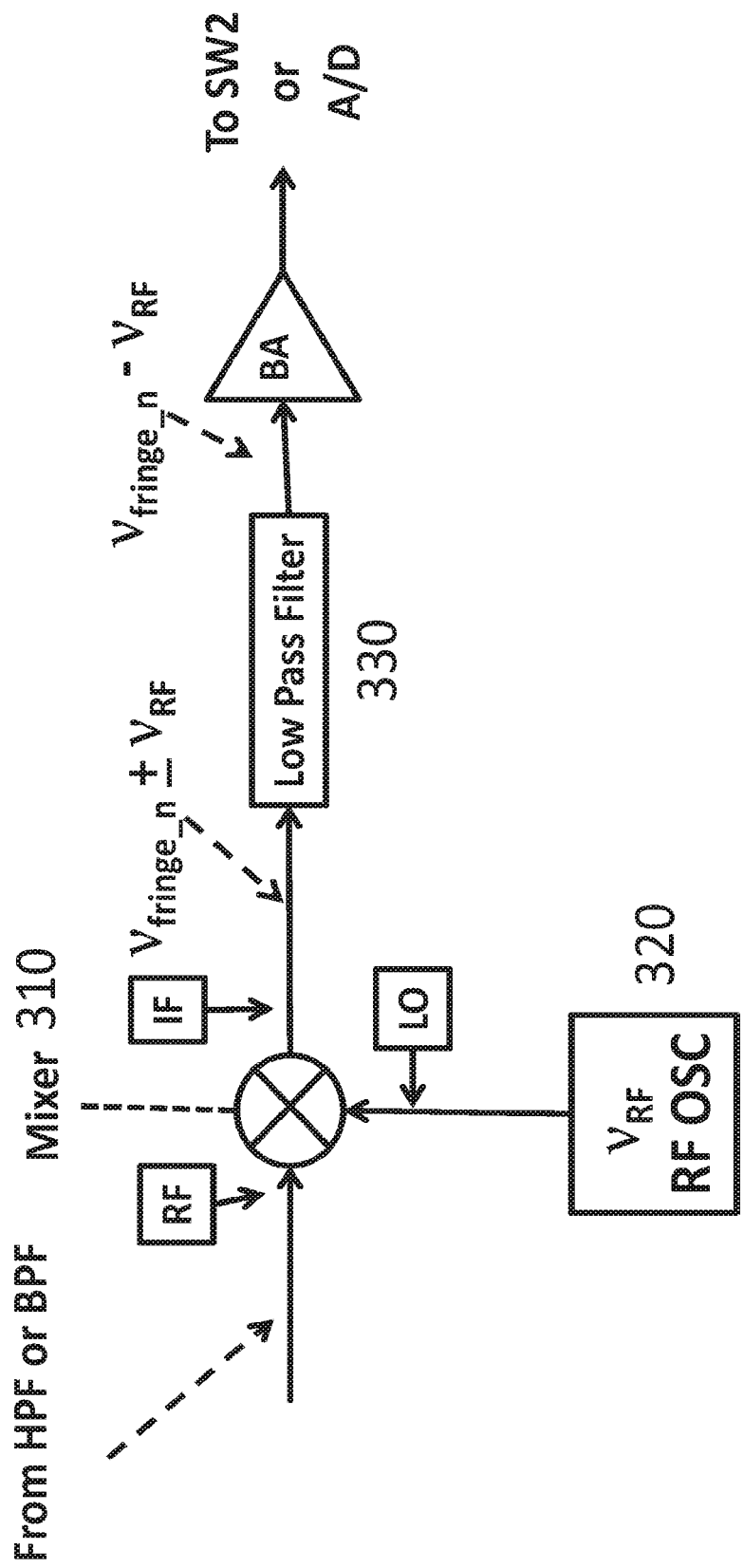
FIG. 3 is a block diagram of a frequency down-shifter system according to an embodiment of the invention.

FIG. 3 is a block diagram of a frequency down-shifter system 250 according to an embodiment of the invention. The frequency down-shifter system 250 may include a mixer 310. The mixer 310 may be a nonlinear electrical circuit that creates new frequencies from signals applied to it. For example, two signals at frequencies $v_1$ and $v_2$ may be applied to a mixer, and the mixer may produce new signals at the sum $v_1+v_2$ and difference $v_1-v_2$ of the original frequencies.

Mixers may be used to shift signals from one frequency range to another, a process known as heterodyning. The use of the new signal at the difference frequency is often called down conversion. An example application of frequency down conversion is the reception of FM radio broadcast signals. These radio signals are broadcast on a carrier frequency centered around 100 MHz, but contain audio information only below 20 KHz. A local oscillator may produce a local signal at the broadcast frequency (the tuner), which may be mixed with the received signal from the antenna. The difference (or down converted) frequency from the tuner may be low pass filtered to isolate the audio content.

When SW1 230 is in position 2, the OCT fringe frequency signals (e.g., as given by Eq. 5) may be directed directly, or through an optional HPF 240 (or band pass filter (BPF)), to the RF input of the mixer 310. The local oscillator (LO) input of the RF mixer 310 may be connected to an RF oscillator 320 operating at a frequency $v_{RF}$. The RF mixer 310 may combine the RF input and LO input, and the RF mixer 310 output signal may be proportional to the product of the time dependences of the RF and the LO input signals, $$V_{mixer}(t)=E_n[V_{mix\_n\_out}\{e^{-i2\pi[v_{fringe\_n}]t}*e^{-i2\pi v_{RF}T}\}], \quad 12)$$

where $V_{mix\_n\_out}$ represents the mixer output voltage that depends upon the mixer input powers and the mixer conversion efficiency. Expanding Eq. 12 may yield, $$V_{mixer}(t)=E_n[V_{mix\_n\_out}(e^{-i2\pi[v_{fringe\_n}-v_{RF}]t}*e^{-i2\pi[v_{fringe\_n}-v_{RF}]t})], \quad 13)$$

where the summation index n is summed over all of the sample spatial elements. The output signal from the mixer 310 may be connected to a low pass filter (LPF) 330 that may prevent the sum frequency components from reaching the A/D converter 280. The output of the LPF 330 may be directed either directly to the A/D converter 280 or through an optional buffer amplifier 270 and then to the A/D converter 280. The down conversion process may shift every OCT fringe frequency down by $v_{RF}$ thus, $$v_{down-converted}=v_{fringe\_n\_max}-v_{RF} \quad 14)$$

For example, if the highest fringe frequency of interest is 2 $BW_{AtoD}$ and, $$v_{RF}=BW_{AtoD} \quad 15)$$

then the entire spectrum may be measured and reconstructed with the above system 200. The result may be a significant reduction of the required A/D sample rate. In summary, frequencies $v_{fringe\_n} \leq v_{RF}$ may be measured when SW1 230 and SW2 260 are both in position 1, and frequencies 2 $BW_{AtoD} \geq v_{fringe\_n} \geq v_{RF}$ may be measured when SW1 230 and SW2 260 are both in position 2. By reducing the highest frequencies to within the sample rates of slower and significantly less expensive analog to digital converters, overall system cost and/or complexity may be reduced.

Figure 4:
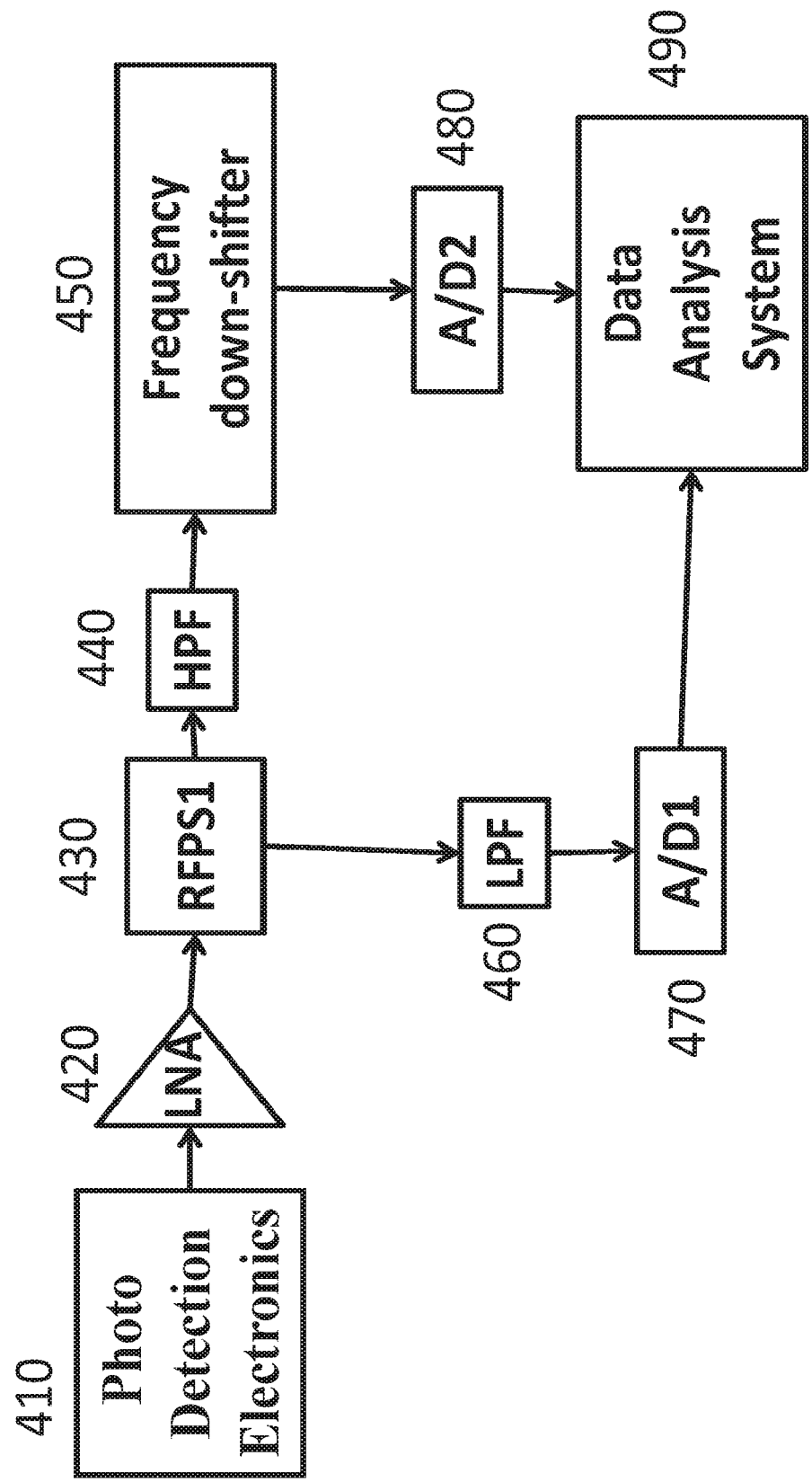
FIG. 4 is a block diagram of a simultaneous dual frequency band down-converter system according to an embodiment of the invention.

FIG. 4 is a block diagram of a simultaneous dual frequency band down-converter system 400 according to an embodiment of the invention. The system 400 may capture the entire OCT fringe frequency spectrum up to 2 $BW_{AtoD}$ in a single A-scan, for example. This system 400 may function differently from the system 200 of FIG. 2, where the low and high frequency spectra are measured in two separate A-scans. In this embodiment the photo detector 410 output signal may be amplified by an optional LNA 420 and then sent to an RF power splitter 430 or may be sent directly to the RF power splitter 430. Each of the outputs of the RF power splitter 430 may be connected to optional amplifiers in some embodiments. The RF power splitter 43 may direct half of the power to a LPF 460 with a high frequency cutoff of $BW_{AtoD}$. The output of the LPF 460 may be connected to a low frequency A/D converter 470. The other output of the RF power splitter 430 may be connected to a HPF 440 whose low frequency cutoff is $BW_{AtoD}$. The HPF 440 may pass frequencies between $BW_{AtoD}$ and 2 $BW_{AtoD}$. The output of the HPF 440 may be directed to a frequency down-shifter 450 that may shift the frequencies down so that the output of the frequency down-shifter 450 is less than or equal to $BW_{AtoD}$. The output of the frequency down-shifter 450 may be directed to the high frequency band A/D converter 480. The DAS 490 may use the output of the low frequency band A/D converter 470 and high frequency band A/D converter 480 to reconstruct the OCT fringe frequency spectrum, taking into account the down-shift of the high frequency band by $v_{RF}$. Using two separate A/D converters may allow the DAS 490 to capture the entire OCT fringe frequency spectrum in a single A-scan. Data may be collected twice as fast as was the case for the sequential scan embodiment 200 presented in FIG. 2. The frequency down-shifter electronics 450 for the simultaneous down-conversion system 400 may be configured in the same way as the frequency down-shifter electronics 250 used in the system 200 of FIG. 2 and shown in detail in FIG. 3. The down-shifter systems 250 and 450 may be identical for the sequential and simultaneous down-converter systems 200 and 400.

Figure 5:
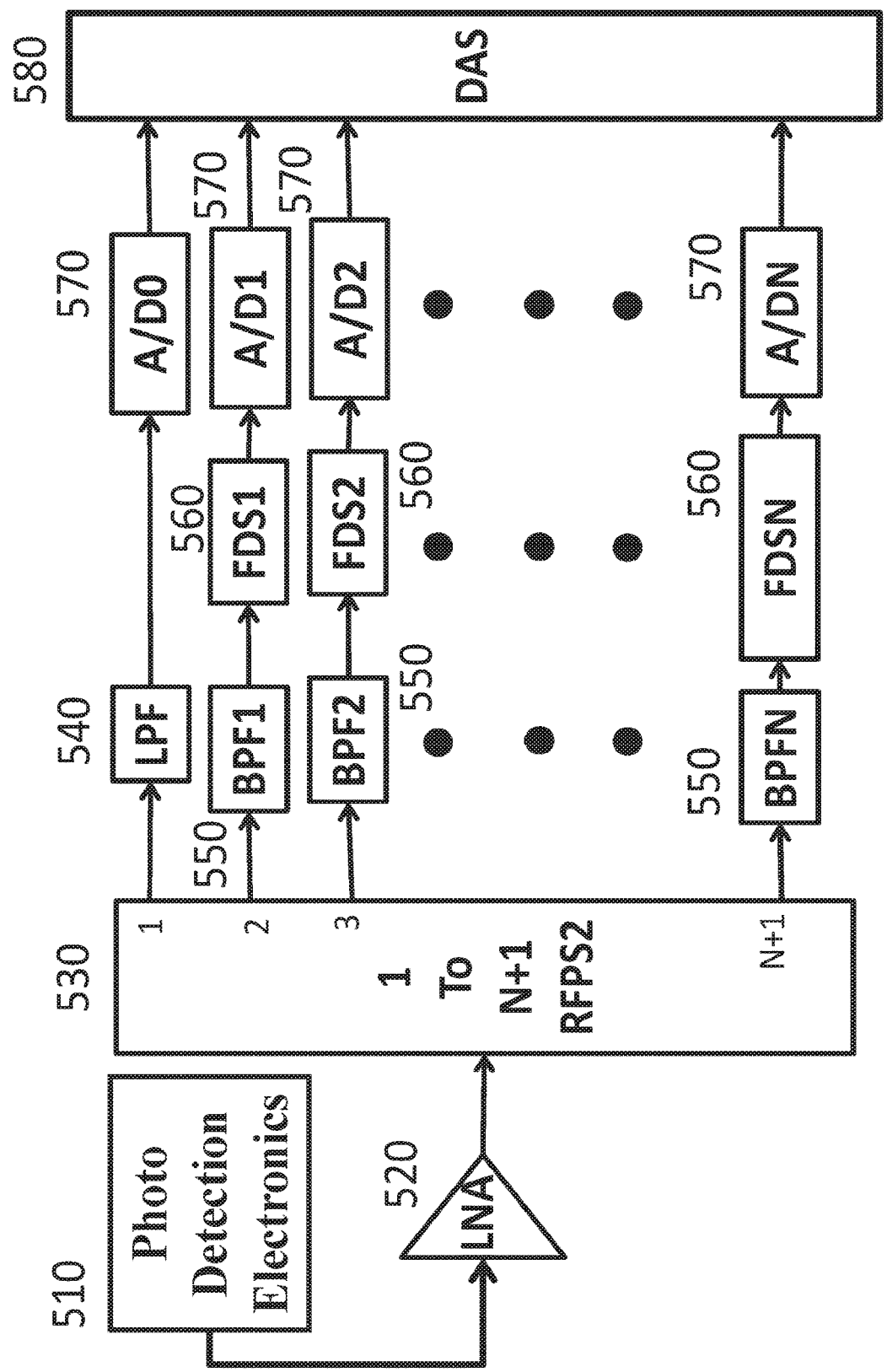
FIG. 5 is a block diagram of a simultaneous multiple frequency band down-converter system according to an embodiment of the invention.

FIG. 5 is a block diagram of a simultaneous multiple frequency band down-converter system 500 according to an embodiment of the invention. In a single A-scan, this system 500 may capture a fringe frequency spectrum spanning, $$0 \leq v_{fringe} \leq (N+1)BW_{AtoD} \quad 16)$$

where N represents the number of down-converter stages required to measure the entire spectrum in a single A-scan. The signal from the photo detection electronics 510 may be directed to an optional LNA 520. The output from the photo detection amplifier 510 or optional LNA 520, if included, may be connected to a 1×(N+1) RF power splitter 530. Each channel illustrated in FIG. 5 may down-shift a unique portion of the OCT spectrum to within the bandwidth of the analog to digital converters, $BW_{AtoD}$.

One of the RF power splitter 530 outputs may be directed to an LPF 540 which may include an optional amplifier. The output of the LPF 540 may be connected to an A/D converter 570. This channel may measure the portion of the fringe spectrum below $BW_{AtoD}$. The other outputs of the RF power splitter 530 may be directed to individual and unique bandpass filters 550 that may include optional amplifiers and that may each output to down-shifter systems 560 having unique down-shifting frequencies. For example, assume that the $(M+1)^{th}$ output of the RF power splitter 530 has a bandpass filter 550 that isolates frequencies between $(M) BW_{AtoD}$ and $(M+1) BW_{AtoD}$. Then, setting the RF oscillation frequency of the $M^{th}$ frequency down-shifter 560, $$v_{RFM} = MBW_{AtoD} \qquad 17)$$

may ensure that the $M^{th}$ A/D 570 will digitize only the portion of the OCT spectrum between $M BW_{AtoD}$ and $(M+1) BW_{AtoD}$. In this manner, when each channel isolates and digitizes a unique portion of the spectrum, the data analysis system 580 may reliably reconstruct the entire OCT frequency spectrum. The multiple parallel channels may provide for simultaneous collection of the entire OCT frequency spectrum in a single A-scan. The data analysis system 580 may accurately reconstruct the spatial distribution of backscattering features, since the acquisition of the entire OCT frequency spectrum can be reconstructed because each of the N A/D converters 570 may receive a signal from $1/(N+1)$ of the original spectrum. Frequency down-shifter systems 560 of this embodiment may be similar to the system 250 of FIG. 3, for example.

Figure 6:
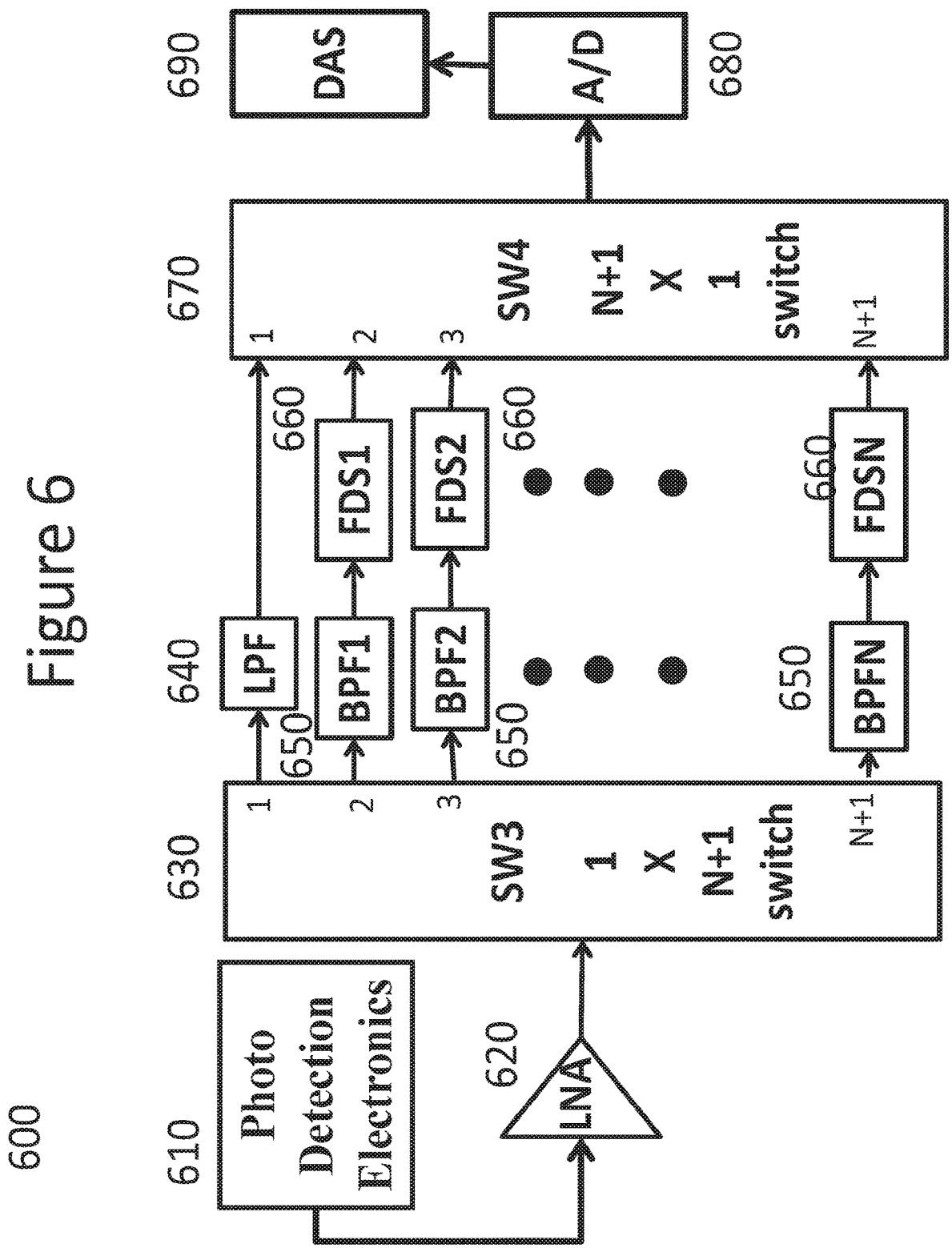
FIG. 6 is a block diagram of a sequential down-converter system according to an embodiment of the invention.

In some applications where maximum speed is not required, a purely sequential embodiment may be used. FIG. 6 is a block diagram of a sequential down-converter system 600 according to an embodiment of the invention. In this embodiment, the photo detection electronics 610 output signal may be amplified by an optional LNA 620 and then sent to an RF 1×(N+1) switch 630 or may be sent directly to the switch 630. Output 1 of the switch 630 may be connected to an LPF 640, which in turn may be connected to input 1 of an RF (N+1)×1 switch 670. Each of the other outputs of the switch 630 may be connected to BPFs 650 which may isolate a unique portion of the OCT fringe frequency spectrum. For example, when switch 630 is in the $(M+1)^{th}$ position, the $(M+1)^{th}$ output may be connected to a bandpass filter 650 that passes frequencies between $M BW_{AtoD}$ and $(M+1) BW_{AtoD}$. The bandpass filter 650 may be connected to the $M^{th}$ frequency down-shifter 660. The RF oscillator of the $M^{th}$ frequency down-shifter 660 may oscillate at frequency, $$v_{RFM} = MBW_{AtoD}. \qquad 18)$$

Thus, the output of the $M^{th}$ frequency down-shifter 660 may be down-converted to between 0 and $BW_{AtoD}$. The output of each frequency down-shifter 660 may be connected to switch 670.

If switch 630 and switch 670 are both in positions M+1, then output of the $M^{th}$ frequency down-shifter 660 may be connected to the A/D converter 680. The output of the A/D converter 680 may be sent to the DAS 690. By sequentially switching switch 630 and switch 670 synchronously through all of the (N+1) channels, the entire OCT fringe frequency spectrum may be collected, and the DAS 690 may reconstruct the original spectrum. Frequency down-shifter systems 660 of this embodiment may be similar to the system 250 of FIG. 3, for example.

Figure 7:
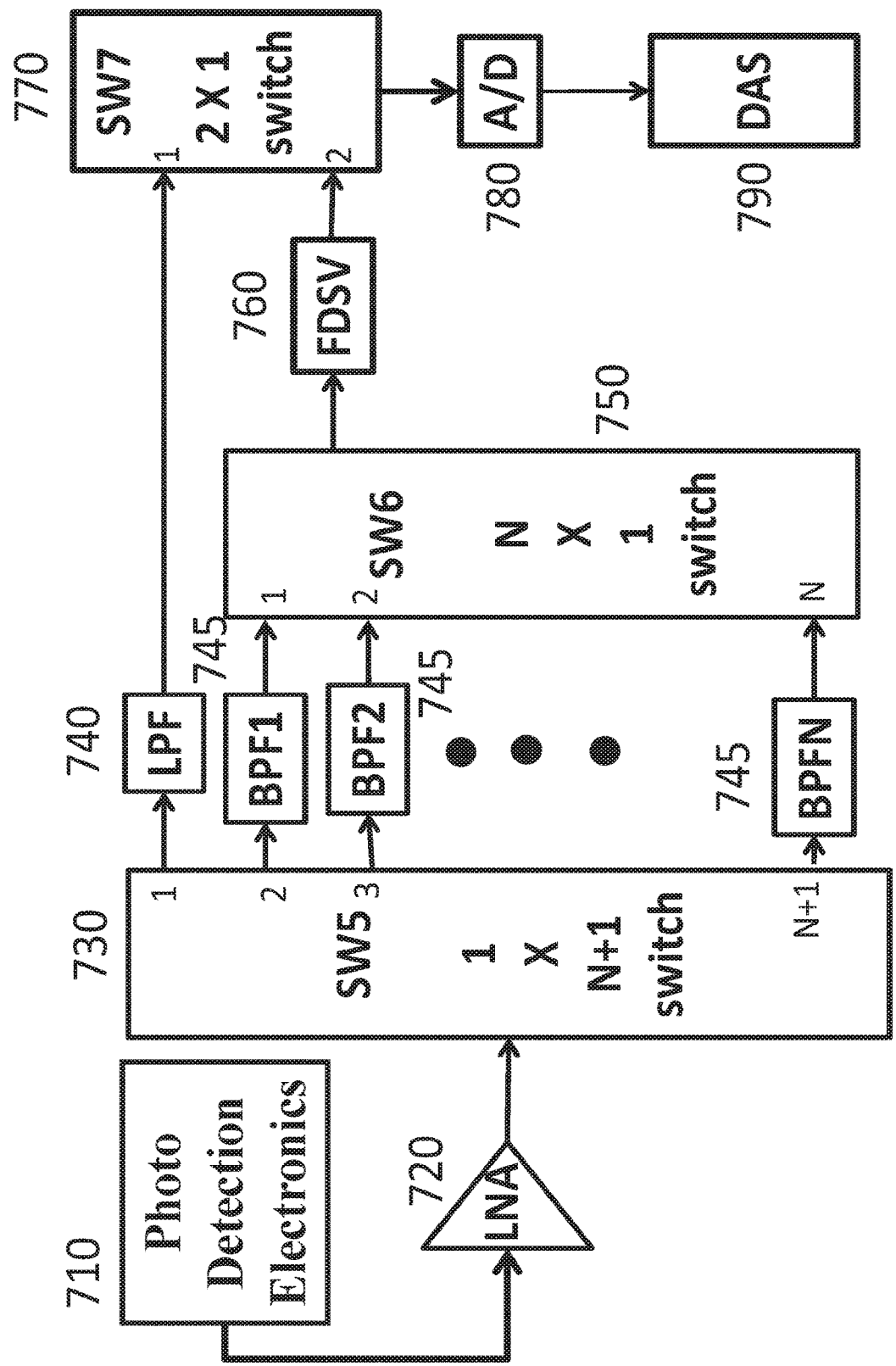
FIG. 7 is a block diagram of a sequential down-converter system according to an embodiment of the invention.

FIG. 7 is a block diagram of a sequential down-converter system 700 according to another embodiment of the invention. In this embodiment, the photo detection electronics 710 output signal may be amplified by an optional LNA 720 and then sent to an RF 1×(N+1) switch 730 or may be sent directly to the switch 730. Output 1 of switch 730 may be connected to an LPF 740. The output of the LPF 740 may be connected directly to input 1 of a 2×1 switch 770. When switch 730 is in position 1, such that the photo detector 710 signal is directly connected to LPF 740, switch 770 may also be in position 1, and the output signal from the LPF 740 may be connected to the A/D converter 780. The fringe frequency spectrum between 0 and $BW_{AtoD}$ may be measured at the A/D converter 780 when the switches 730 and 770 are both in position 1.

Each output of switch 730 other than position 1 may be connected to a BPF 745 which may isolate a unique portion of the OCT fringe frequency spectrum. For example, when switch 730 is in the $(M+1)^{th}$ position, the output signal from the optional low noise amplifier 720 or photo detection electronics 710 may be connected to the $M^{th}$ BPF 745 that passes frequencies between $M BW_{AtoD}$ and $(M+1) BW_{AtoD}$. The $M^{th}$ BPF 745 may be connected to the $M^{th}$ position of the N×1 switch 760. When switch 760 is in position M, the output of the $M^{th}$ BPF 745 may be connected through switch 760 to the variable frequency down-shifter 760. Under those conditions, the variable frequency down-shifter system 760 may be switched to down-shift frequencies between $M BW_{AtoD}$ and $(M+1) BW_{AtoD}$ to within the bandwidth of the A/D converter 780, $BW_{AtoD}$. The output of the variable frequency down-shifter system 760 may be connected to position 2 of switch 770. When switch 730 is in a position other than position 1, switch 770 may be set to position 2 so that the output of the frequency down-shifter 760 may be connected to the A/D converter 780. The output of the A/D converter 780 may be connected to the DAS 790. The fringe frequency spectrum between $M BW_{AtoD}$ and $(M+1) BW_{AtoD}$ may be down-converted to the A/D bandwidth and measured by the A/D converter 780 when switch 730 is set to the $(M+1)^{th}$ position, switch 750 is set to the $M^{th}$ position, switch 770 is set to position 2, and the frequency down-shifter 760 is set to down-shift by a frequency of $M BW_{AtoD}$. In this manner, the entire fringe frequency spectrum may be acquired and reconstructed in N+1 sequential A-scans.

Figure 8:
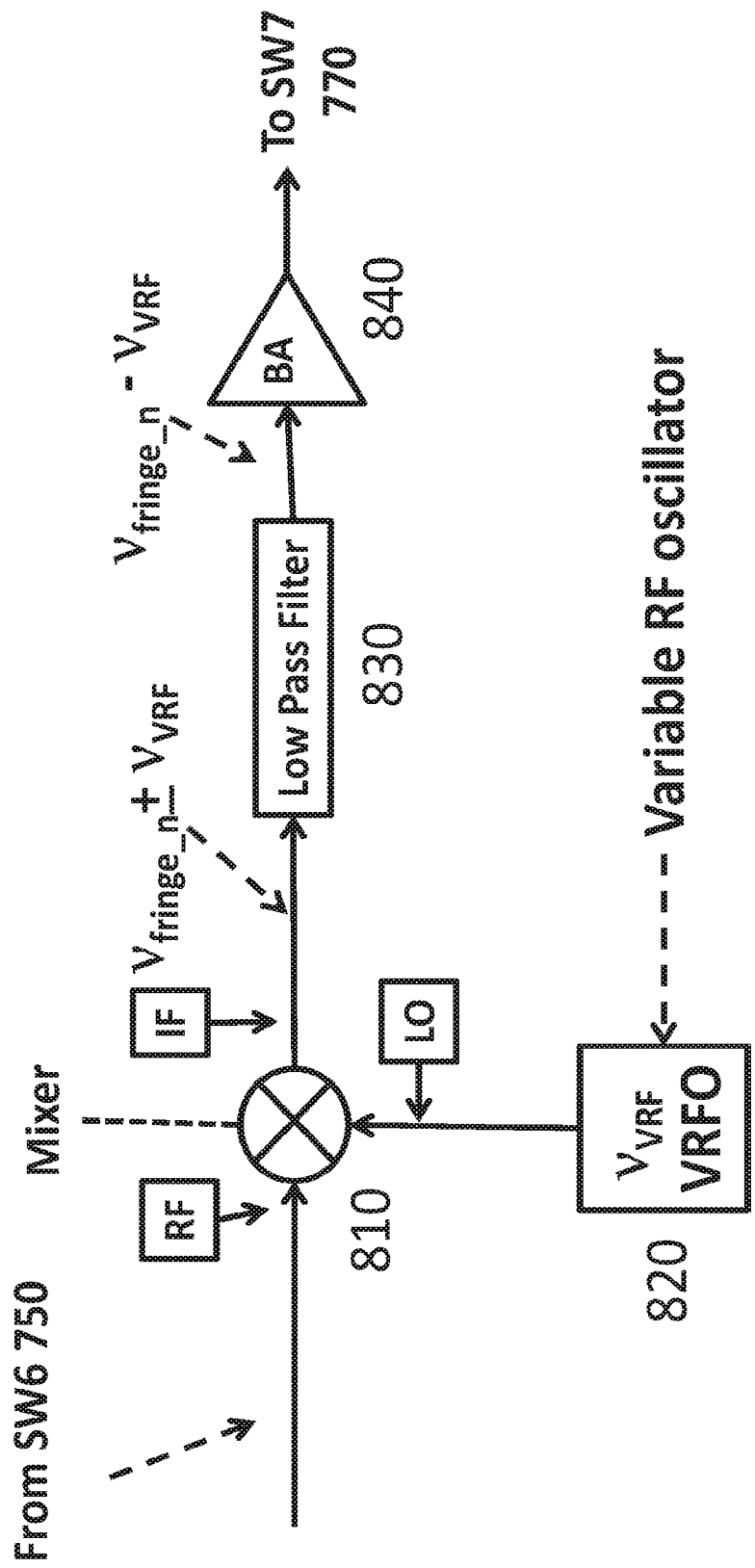
FIG. 8 is a block diagram of a variable frequency down-shifter system according to an embodiment of the invention.

FIG. 8 is a block diagram of a variable frequency down-shifter system 760 according to an embodiment of the invention, for example the variable frequency down-shifter system 760 used in the system 700 of FIG. 7. The variable frequency down-shifter system 760 may include a mixer 810. The RF input signal to the mixer 810 may come from switch 750 when the variable frequency down-shifter system 760 is used in the system 700 of FIG. 7, for example. The local oscillator input to the mixer 810 may be connected to a variable frequency RF oscillator 820. The frequency of the variable frequency RF oscillator 820 may be set to down-shift the RF input signal to between 0 and $BW_{AtoD}$. For example, if switch 730 is in the M+1 position and switch 750 is in the $M^{th}$ position, the fringe frequency signal may be filtered through the $M^{th}$ BPF 745 so that only frequencies between $M BW_{AtoD}$ and $(M+1) BW_{AtoD}$ reach the RF input of the mixer 810. In that case the variable frequency RF oscillator 820 may be set to oscillate at a frequency, $$v_{VRF} = MBW_{AtoD}. \qquad 19)$$

The output frequencies at the mixer 810 output IF may be the sum and difference frequencies of the mixer 810 RF and LO inputs. The LPF 830 may eliminate the sum frequencies, leaving only frequencies below $BW_{AtoD}$. The output frequencies of the variable frequency down-shifter 760 may always be between 0 and $BW_{AtoD}$, provided that the switch settings and variable frequency oscillator 820 frequencies are set in the manner described above. The output of the LPF 830 may be directed either directly to the switch 770 or through an optional buffer amplifier 840 and then to the switch 770.

Figure 9:
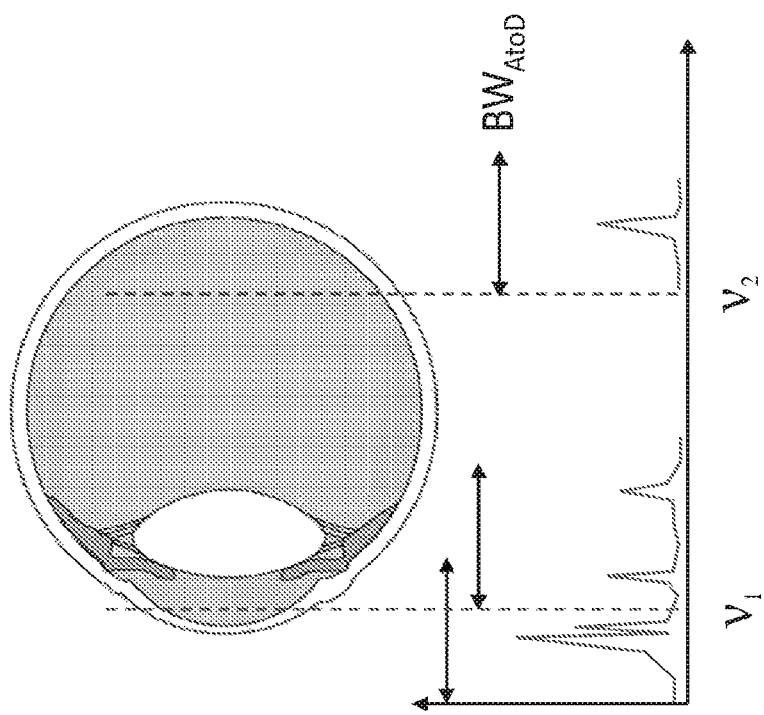
FIG. 9 illustrates an example down conversion application according to an embodiment of the invention.

FIG. 9 illustrates an example down conversion application according to an embodiment of the invention. The above described down conversion systems and methods may be applied to measurements of the human eye. In this case, the lowest OCT fringe frequencies may be produced from scattering in the cornea, with successively greater frequencies associated with the anterior and posterior lens and retina. As noted in equation 10, the highest frequencies may be up to 1.7 GHz for a human eye, however all the signals may be down converted and captured using 0.5 Gsps ($BW_{AtoD}$=0.5 GHz) analog to digital converters. The eye may be positioned so the corneal signal is located in the frequency range 0 to $BW_{AtoD}$, which may be digitized faithfully by the selected analog to digital converter. The signals from the anterior and posterior lens surfaces may be down converted by mixing with a local signal at frequency $v_1$ and brought into the analog to digital converter range 0 to $BW_{AtoD}$. Likewise, the retinal signal may be down converted by mixing with a local signal at frequency $v_2$.

While various embodiments have been described above, it should be understood that they have been presented by way of example and not limitation. It will be apparent to persons skilled in the relevant art(s) that various changes in form and detail can be made therein without departing from the spirit and scope. In fact, after reading the above description, it will be apparent to one skilled in the relevant art(s) how to implement alternative embodiments. For example, hybrid approaches may be employed wherein the number of sequential scans may be reduced by performing a number of simultaneous scans in each of the sequential scans. In such a hybrid approach, a number L of simultaneous scans may be performed in each of the sequential scans, thus reducing the number of sequential scans by ~1/L. The hybrid approach may be used with a combination of either of the multiple sequential scan embodiments of FIGS. 6 and 7 and a multiple simultaneous scan approach of L elements.

In addition, it should be understood that any figures that highlight the functionality and advantages are presented for example purposes only. The disclosed methodology and system are each sufficiently flexible and configurable such that they may be utilized in ways other than that shown. For example, in addition to being used in SS-OCT systems, such as system 100 to shift photo detection output frequencies, the above-described frequency shifting embodiments may be used to shift the frequency of other signals in other systems to frequencies appropriate for A/D conversion. All patents and patent applications cited herein are hereby incorporated by reference in their entirety.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

While certain illustrated embodiments of this disclosure have been shown and described in an exemplary form with a certain degree of particularity, those skilled in the art will understand that the embodiments are provided by way of example only, and that various variations can be made without departing from the spirit or scope of the invention. Thus, it is intended that this disclosure cover all modifications, alternative constructions, changes, substitutions, variations, as well as the combinations and arrangements of parts, structures, and steps that come within the spirit and scope of the invention as generally expressed by the following claims and their equivalents.

Finally, it is the applicant's intent that only those claims that include the express language "means for" or "step for" be interpreted under 35 U.S.C. 112(f). Claims that do not expressly include the phrase "means for" or "step for" are not to be interpreted under 35 U.S.C. 112(f).

What is claimed is:

1. A system, comprising:
   a swept source laser configured to output light having a frequency which is swept over time;
   a beamsplitter configured to receive the light and to supply a first portion of the light to a reference path and a second portion of the light to a sample path;
   a beam combiner having a first input, a second input, and an output, wherein the first input is configured to receive first portion of the light from the reference path;
   optics disposed in the sample path and configured to direct the second portion of the light to a sample and to direct backscattered light from the object to the second input of the beam combiner;
   a photo detection device configured to receive from the beam combiner the first portion of the light from the reference path and the backscattered light from the sample and to output an electrical signal produced by interference between a first optical field of the first portion of the light from the reference path and a second optical field of the backscattered light from the sample, wherein the electrical signal comprises a first frequency component at or below a set frequency and a second frequency component above the set frequency; and
   a signal processor comprising:
      an analog-to-digital conversion subsystem comprising at least a first analog-to-digital converter (ADC);
      a frequency down shifter; and
      a distribution element configured to receive the electrical signal output by the photo detection device, to send the first frequency component to the analog-to-digital conversion subsystem, and to send the second frequency component to the frequency down shifter, wherein the frequency down shifter is configured to down shift the second frequency component to a downshifted frequency at or below the set frequency to form a down shifted second frequency component, and to send the down shifted second frequency component to the analog-to-digital conversion subsystem.

2. The system of claim 1, wherein the first ADC has a maximum conversion frequency and the set frequency is less than or equal to the maximum conversion frequency.

3. The system of claim 1, wherein the distribution element comprises a switch having a first output and a second output, wherein the distribution element is configured to:
    switch the electrical signal output by the photo detection device to the first output to pass the first frequency component to the first ADC during a first scan of the sample; and
    switch the electrical signal output by the photo detection device to the second output to pass the second frequency component to the frequency down shifter during a second scan of the sample.

4. The system of claim 3, wherein the signal processor further comprises a bandpass filter or a highpass filter coupled between the second output of the switch and an input of the frequency down shifter.

5. The system of claim 4, wherein the signal processor further comprises a second switch coupled to the first output of the switch and an output of the frequency down shifter, the second switch being configured to send an output of the second switch to the first ADC.

6. The system of claim 1, wherein the distribution element comprises a splitter configured to substantially simultaneously send the electrical signal output by the photo detection device to the first ADC and to the frequency down shifter.

7. The system of claim 6, further comprising a bandpass filter or a lowpass filter coupled between an output of the splitter and an input of the first ADC.

8. The system of claim 6, further comprising a bandpass filter or a highpass filter coupled between an output of the splitter and an input of the frequency down shifter.

9. The system of claim 6, wherein:
    the analog-to-digital conversion subsystem further comprises a second ADC; and
    the down shifted second frequency component is sent is to the second ADC.

10. The system of claim 1, wherein the frequency down shifter comprises:
    a local oscillator configured to generate a local oscillator signal;
    a mixer having a first input configured to receive the second frequency component and a second input configured to receive the local oscillator signal, wherein the mixer is configured to mix the second frequency component and the local oscillator signal to form an intermediate output signal; and
    a lowpass filter or a bandpass filter coupled to an output of the mixer and configured to filter the intermediate output signal to produce the down shifted second frequency component.

11. A system, comprising:
    a plurality of filters;
    a plurality of analog-to-digital converters (ADCs);
    a plurality of frequency down shifters; and
    a distribution element comprising an radio frequency (RF) splitter having an input configured to receive an electrical signal output by a photo detection device and having a plurality of outputs further configured to substantially simultaneously send the electrical signal to each of the plurality of filters,
    wherein at least a first filter among the plurality of filters comprises a lowpass filter or a bandpass filter coupled between a first output of the RF splitter and an input of a first one of the ADCs,
    wherein at least a second filter and a third filter among the plurality of filters each comprise a highpass filter or a bandpass filter, each of the second filter and third filter being coupled between a separate output of the RF splitter and a corresponding one of the frequency down shifter, and
    wherein each of the frequency down shifters has an output coupled to a corresponding one of the ADCs.

12. The system of claim 11, wherein each of the frequency down shifters is configured to shift a corresponding frequency component of the electrical signal.

13. The system of claim 11, wherein each of the filters is configured to pass a different frequency component of the electrical signal.

14. The system of claim 11, wherein each of the frequency down shifters comprises:
    a local oscillator configured to generate a local oscillator signal;
    a mixer having a first input configured to receive an input signal to the frequency down shifter and a second input configured to receive the local oscillator signal, wherein the mixer is configured to mix the input signal and the local oscillator signal to form an intermediate output signal; and
    a lowpass filter or a bandpass filter coupled to an output of the mixer and configured to filter the intermediate output signal.

15. The system of claim 11, further comprising a low noise amplifier having an input configured to receive the electrical signal output by the photo detection device, to amplify the electrical signal output by the photo detection device, and to supply the amplified electrical signal output by the photo detection device to the input of the RF splitter.

16. A system, comprising:
    a plurality of filters;
    an analog-to-digital converter (ADC);
    a plurality of frequency down shifters; and
    a distribution element, comprising:
        a first switch having an input configured to receive an electrical signal output by a photo detection device, and further having a plurality of outputs each connected to a corresponding one of the plurality of filters, wherein the first switch is configured to sequentially send the electrical signal via the plurality of outputs to each of the plurality of filters; and
        a second switch having a plurality of inputs, and further having an output coupled to the ADC,
    wherein at least one of the filters comprises a lowpass filter or a bandpass filter coupled between a first one of the outputs of the first switch and a first one of the inputs of the second switch,
    wherein at least a second filter and a third filter among the plurality of filters each comprise a highpass filter or a bandpass filter, wherein each of the second filter and third filter is coupled between a corresponding one of the plurality of outputs of the first switch and a corresponding one of the plurality of frequency down shifters,
    wherein each of the frequency down shifters has an output coupled to a corresponding one of the plurality of inputs of the second switch, and wherein the second switch is configured to sequentially connect each of the plurality of second switch inputs to the ADC.

17. The system of claim 16, wherein each of the frequency down shifters is configured to shift a corresponding frequency component of the electrical signal.

18. The system of claim 16, wherein each of the filters is configured to pass a different frequency component of the electrical signal.

19. The system of claim 16, wherein each of the frequency down shifters comprises:
   a local oscillator configured to generate a local oscillator signal;
   a mixer having a first input configured to receive an input signal to the frequency down shifter and a second input configured to receive the local oscillator signal, wherein the mixer is configured to mix the input signal and the local oscillator signal to form an intermediate output signal; and
   a lowpass filter or a bandpass filter coupled to an output of the mixer and configured to filter the intermediate output signal.

20. The system of claim 16, further comprising a low noise amplifier having an input configured to receive the electrical signal output by the photo detection device, to amplify the electrical signal output by the photo detection device, and to supply the amplified electrical signal output by the photo detection device to the input of the first switch.

* * * * *